United States Patent [19]

Head

[11] 4,014,331
[45] Mar. 29, 1977

[54] SYRINGE BARREL WITH PROTECTIVE PLASTIC COVER

[76] Inventor: James E. Head, R.R. 5, Hereford, Tex. 79045

[22] Filed: Dec. 30, 1975

[21] Appl. No.: 645,479

[52] U.S. Cl. ............................ 128/224; 128/218 D
[51] Int. Cl.² ......................................... A61M 3/00
[58] Field of Search .......... 128/224, 234, 236, 235, 128/215, 216, 218 R, 218 A, 218 G, 218 D, 218 DA, 218 C, 220, 221, 214.4, DIG. 18; 264/342; 29/447, DIG. 35

[56] References Cited

UNITED STATES PATENTS

| | | | |
|---|---|---|---|
| 2,417,140 | 3/1947 | Swanson | 128/224 |
| 2,624,338 | 1/1953 | Moore et al. | 128/218 D |
| 3,160,156 | 12/1964 | Tyler | 128/236 |
| 3,406,685 | 10/1968 | May | 128/214.4 |
| 3,712,301 | 1/1973 | Sarnoff | 128/218 D |
| 3,720,211 | 3/1973 | Kyrias | 128/215 |

*Primary Examiner*—John D. Yasko
*Attorney, Agent, or Firm*—Clarence A. O'Brien; Harvey B. Jacobson

[57] ABSTRACT

A syringe assembly of the type including a frangible open ended tubular barrel snugly received within a longitudinally slotted tubular body including at least partial end walls between which the barrel is received has its longitudinally slotted tubular body enclosed within a thick walled cylindrical sleeve constructed of translucent plastic material. The sleeve is initially heated to effect its expansion and thereafter telescoped over the longitudinally slotted tubular body of the syringe and allowed to cool so as to shrink tightly about the body to cover the slotted portions thereof from the exterior of the body.

6 Claims, 3 Drawing Figures

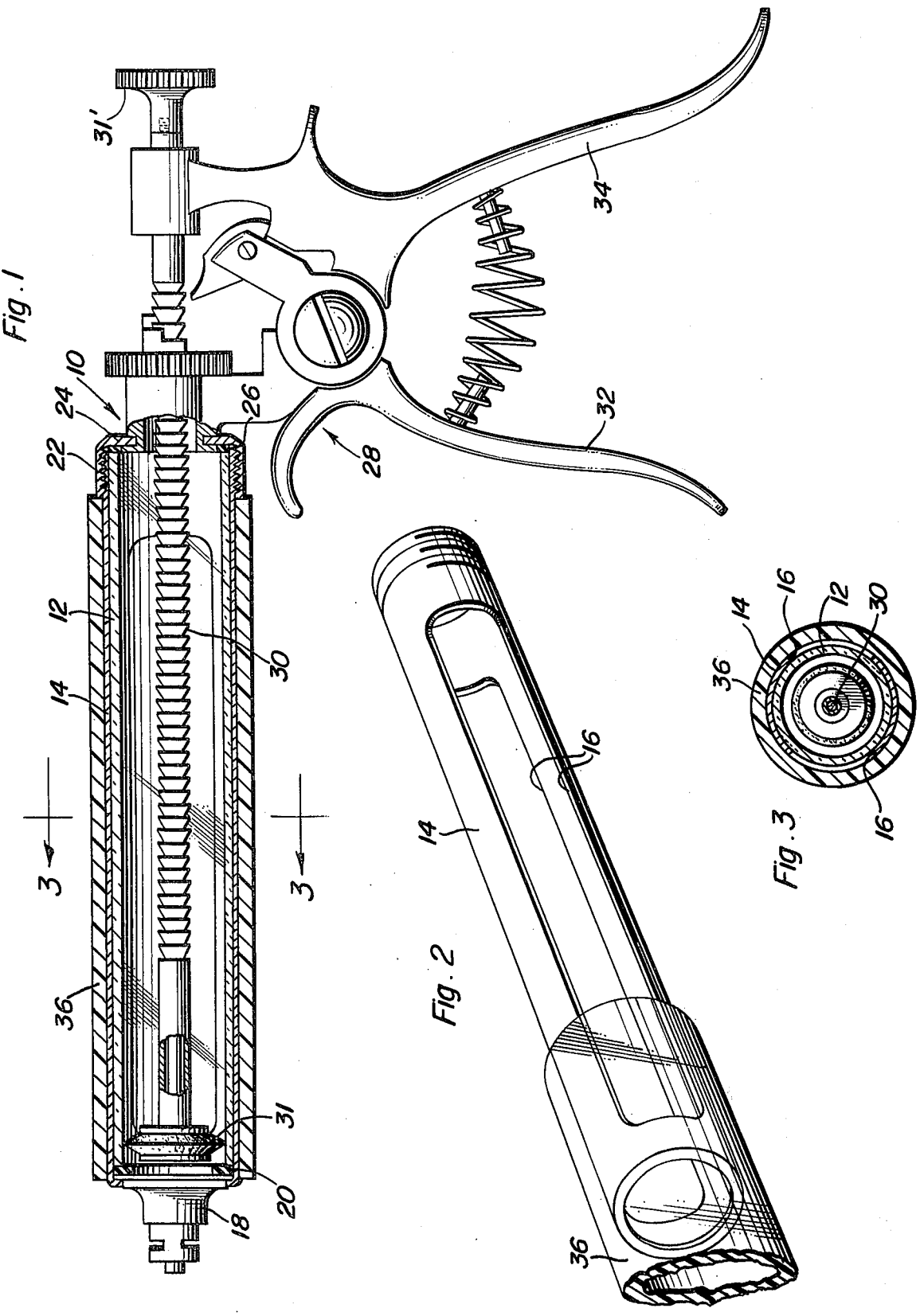

SYRINGE BARREL WITH PROTECTIVE PLASTIC COVER

BACKGROUND OF THE INVENTION

Syringes including frangible barrels of the replaceable type are used extensively in the livestock industry for the purpose of vaccinating livestock. The frangible syringe barrels are subject to frequent breakage during a day's use and breakage of the barrel not only requires its replacement at considerable cost but also interrupts the vaccinating operation with the resultant loss in time of many persons involved in a large scale vaccinating operation. In addition, breakage of the frangible barrel can also result in damage to the piston defining O-ring of the syringe as well as various sealing O-rings thereof and necessitate their replacement at additional cost.

Various forms of syringes suitable for large scale vaccinating operations have been heretofore designed, but those provided with frangible syringe barrels do not include sufficient means for protecting the frangible barrels against breakage.

Examples of various forms of syringes including some of the structural features of the basic syringe structure of the instant invention are disclosed in U.S. Pat. Nos. 3,160,156 and 3,797,489.

BRIEF DESCRIPTION OF THE INVENTION

The syringe assembly for the use in vaccinating livestock is provided with a frangible barrel enclosed within a longitudinally slotted tubular body and the barrel is subject to breakage by the inpact of foreign objects therewith. The protective sleeve of the instant invention comprises a thick walled cylindrical sleeve constructed of plastic material and is expandable upon heating and shrinkable upon subsequent cooling. The sleeve is initially heated and telescoped over the slotted body of the syringe and thereafter allowed to cool for tightly shrinking about the body in a position covering the slotted portions thereof and thus protecting the frangible barrel disposed within the body.

The main object of this invention is to provide a means whereby the frangible barrel of a livestock vaccinating syringe may be protected against breakage.

Another object of this invention, in accordance with the immediately preceding object, is to provide an improved livestock vaccinating syringe having protection therefor against breakage of the frangible barrel thereof and which thereby reduces the cost of replaceable barrels and the loss in man-hours required when a broken glass barrel has to be replaced.

Still another object of this invention is to provide an improved livestock vaccinating syringe assembly with the frangible barrel thereof protected against breakage and fully enclosed so as to eliminate the possibility of the operator of the syringe being cut as a result of breakage of the glass barrel.

Another important object of this invention is to provide a livestock vaccinating syringe including means for protecting the glass barrel thereof against breakage and thereby reducing the loss of vaccine as a result of a broken barrel.

A final object of this invention to be specifically enumerated herein is to provide a livestock vaccination syringe with exterior protection for the glass barrel thereof against breakage and through the utilization of structure which will conform to conventional forms of manufacture, be easy to install and long lasting so as to provide a device that will be economically feasible and relatively trouble free in installation.

These together with other objects and advantages which will become subsequently apparent reside in the details of construction and operation as more fully hereinafter described and claimed, reference being had to the accompanying drawings forming a part thereof, wherein like numeral refer to like parts throughout.

BRIEF DESCRIPTION OF THE DRAWINGS

FIG. 1 is a side elevational view of a conventional form of livestock vaccinating syringe with the barrel portion thereof illustrated in longitudinal section and the protective cover of the instant invention snugly telescoped over the longitudinally slotted body of the barrel portions;

FIG. 2 is a fragmentary perspective view illustrating the manner in the which the protective sleeve of the instant invention is longitudinally telescoped over the slotted body of the syringe after the protective sleeve has been heated; and FIG. 3 is a transverse sectional view taken substantially upon the plane indicated by the section line 3—3 of FIG. 1.

DETAILED DESCRIPTION OF THE INVENTION

Referring now more specifically to the drawings the numeral 10 generally designates the conventional form of livestock vaccinating syringe. The syringe 10 includes a frangible cylindrical barrel 12 constructed of glass or nylon snugly telescoped within a cylindrical body 14 having opposite side longitudinal slots 16 formed therein. The body 14 has a front end wall fitting 18 seated in the forward end thereof and an O-ring 20 is disposed between the fitting 18 and the forward end of the frangible barrel 12. In addition, the rear end of the body 14 has a fitting 22 removably threaded thereover and defining a partial rear end wall 24, an O-ring 26 being disposed between the end wall 24 and the rear end of the barrel 12.

The fitting 22 is tubular and supports a hand grip assembly 28 therefrom. The fitting 22 also slidably receives a piston rod assembly 30 therethrough including an axially compressible and radially expandable O-ring 31 defining a piston on the forward end of the assembly 30, the rear end of the assembly including a threaded thumb nut 31' by which the O-ring 31 may be variably compressed so as to be properly radially expanded into sliding engagement with the inner surface of the barrel 12.

The foregoing comprises a description of a conventional form of syringe utilized in vaccinating livestock. The handle assembly 28 may be adjusted so as to forwardly displace the piston assembly 30 the desired amount each time the lever portions 32 and 34 of the handle assembly 28 are squeezed together and throughout a day of normal operation the frangible barrel 12, constructed either of glass or nylon, may become broken several times resulting in the necessity to replace the barrel and also the loss of any vaccine therein. Still further, breakage of the barrel 12 may cause the operator the syringe 10 to be cut.

In order to protect the barrel 12 and also the body 14, a thick walled sleeve 36 is provided. The sleeve 36 is constructed of plastic material which expands when heated and subsequently contracts when allowed to cool. The sleeve 36 has an inside diameter slightly smaller than the outside diameter of of the body 14 and the syringe 10 is disassembled to separate the body 14 from the remainder of the syringe 10. Thereafter, the sleeve 36 is heated in order that its inside diameter will be greater than the outside diameter of the body 14 and the sleeve 36 is then telescoped over the body 14 to the position thereof illustrated in FIG. 1. Thereafter, the sleeve 36 is allowed to cool and shrink tightly about the body 14. Thereafter the syringe 10 may be reassembled with the frangible barrel 12 received within the body 14. Of course, the sleeve 36 covers the slots 16 from the exterior of the body 14 and thereby prevents the glass barrel 12 from being broken as a result of foreign objects impacting with the barrel 12 through the slots 16. Still further, the thick walled construction of the sleeve 36 also protects the body, which is constructed of metal, and prevents sharp with foreign objects from causing the body 14 to be dented and thus the barrel 12 to be broken by deformation of the body 14 as a result of impact with an object.

Inasmuch as the sleeve 36 extends substantially the full length of the barrel 12 except for the portion thereof having the fitting 22 threaded thereover, the barrel 12 is fully protected against impact with a foreign object and breakage of the barrel 12 is substantially eliminated.

Although the syringe 10 illustrated is of the pistol grip type, it is to be understood that other types of syringes are also used for vaccinating livestock and that at least some of these non-pistol grip type syringes also utilize frangible barrels such as the barrel 12 which may benefit from the use of the protective sleeve of the instant invention.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination with a syringe assembly of the type including a frangible open ended tubular barrel snugly received within a longitudinally slotted tubular body including at least partial end walls between which said barrel is received, a thick walled cylindrical sleeve constructed of plastic material expandable upon heating and shrinkable upon subsequent cooling, said sleeve being telescoped over and tightly shrunk about said body to cover the slotted portions thereof from the exterior of said body, said sleeve serving to protect said barrel from breakage as a result of impact with an object through said slotted portions and said body against impact with an object.

2. The combination of claim 1 wherein said sleeve encloses said body substantially fully throughout its length between the opposite end portions thereof.

3. The combination of claim 1 wherein said body is constructed of metal.

4. The combination of claim 1 wherein said sleeve is constructed of translucent material.

5. The method of protecting a frangible syringe barrel snugly enclosed within a longitudinally slotted metal body, said method comprising heating a thick walled plastic cylindrical sleeve to expand the latter, telescoping the heated sleeve over said body to enclose the slotted portions of said body, and allowing said sleeve to cool and thereby shrink tightly about said body.

6. The combination of claim 1 wherein said sleeve encloses said body substantially fully throughout its length between the opposite end portions thereof, said body is constructed of metal, and said sleeve is constructed of translucent material.

* * * * *